United States Patent
Adachi

(10) Patent No.: US 9,974,431 B2
(45) Date of Patent: May 22, 2018

(54) IMAGE SENSOR, IMAGING DEVICE, ENDOSCOPE, AND ENDOSCOPE SYSTEM

(71) Applicant: OLYMPUS CORPORATION, Tokyo (JP)

(72) Inventor: Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/090,905

(22) Filed: Apr. 5, 2016

(65) Prior Publication Data
US 2016/0213238 A1    Jul. 28, 2016

Related U.S. Application Data

(63) Continuation of application No. PCT/JP2015/056678, filed on Mar. 6, 2015.

(30) Foreign Application Priority Data

Jul. 2, 2014 (JP) ................................ 2014-137103

(51) Int. Cl.
H04N 9/64 (2006.01)
H04N 3/14 (2006.01)
(Continued)

(52) U.S. Cl.
CPC .......... *A61B 1/051* (2013.01); *A61B 1/00009* (2013.01); *H04N 5/2256* (2013.01);
(Continued)

(58) Field of Classification Search
CPC ....... H04N 5/378; H04N 5/361; H04N 5/3745
See application file for complete search history.

(56) References Cited

U.S. PATENT DOCUMENTS 5,677,527 A * 10/1997 Cheng .................... H04N 1/401
250/208.1
5,942,774 A   8/1999 Isogai et al.
(Continued)

FOREIGN PATENT DOCUMENTS

CN    101420509 A    4/2009
CN    103053155 A    4/2013
(Continued)

OTHER PUBLICATIONS

International Search Report dated Apr. 14, 2015 issued in PCT/JP2015/056678.
(Continued)

*Primary Examiner* — Rebecca Volentine
(74) *Attorney, Agent, or Firm* — Scully, Scott, Murphy & Presser, P.C.

(57) ABSTRACT

An image sensor includes: a reference signal generation unit configured to generate and output a reference signal in accordance with a predetermined voltage; a plurality of pixels disposed in a two-dimensional matrix form and configured to receive light from outside, and to generate and output an imaging signal in accordance with an amount of the received light; a transfer unit configured to transfer the reference signal output from the reference signal generation unit and the imaging signal output from each of the plurality of pixels, during different periods; and an output unit configured to separately hold the reference signal and the imaging signal transferred from the transfer unit, sequentially switch between the reference signal and the imaging signal to output the switched signal.

9 Claims, 11 Drawing Sheets

(51) Int. Cl.
| | |
|---|---|
| *H04N 5/335* | (2011.01) |
| *A61B 1/05* | (2006.01) |
| *H04N 5/361* | (2011.01) |
| *H04N 5/376* | (2011.01) |
| *A61B 1/00* | (2006.01) |
| *H04N 5/225* | (2006.01) |
| *H04N 5/357* | (2011.01) |

(52) U.S. Cl.
CPC ............ *H04N 5/357* (2013.01); *H04N 5/361* (2013.01); *H04N 5/376* (2013.01); *H04N 5/3765* (2013.01); *H04N 2005/2255* (2013.01)

(56) References Cited

U.S. PATENT DOCUMENTS

| | | | |
|---|---|---|---|
| 7,952,634 B2 | 5/2011 | Noda et al. | |
| 8,710,422 B2 | 4/2014 | Arii et al. | |
| 2003/0025816 A1* | 2/2003 | Sakuragi | H04N 5/3653 348/301 |
| 2003/0052982 A1* | 3/2003 | Chieh | H04N 3/1568 348/302 |
| 2005/0151677 A1* | 7/2005 | Chou | H03G 3/3084 341/122 |
| 2006/0007329 A1* | 1/2006 | Panicacci | H04N 1/409 348/241 |
| 2006/0050161 A1* | 3/2006 | Inagaki | H04N 5/3577 348/300 |
| 2008/0303705 A1* | 12/2008 | Sakakibara | H03M 1/0658 341/172 |
| 2009/0109312 A1 | 4/2009 | Noda et al. | |
| 2009/0278983 A1 | 11/2009 | Azuma et al. | |
| 2010/0053379 A1* | 3/2010 | Willassen | H04N 3/1568 348/241 |
| 2010/0134671 A1* | 6/2010 | Tezuka | H04N 5/217 348/302 |
| 2011/0019039 A1* | 1/2011 | Ikuma | H04N 5/357 348/246 |
| 2011/0261177 A1* | 10/2011 | Moore | H04N 5/361 348/65 |
| 2011/0309235 A1* | 12/2011 | Yoshida | H03M 1/1023 250/208.1 |
| 2012/0035419 A1* | 2/2012 | Ashida | A61B 1/00009 600/109 |
| 2012/0105695 A1* | 5/2012 | Iida | H03G 5/28 348/301 |
| 2012/0113306 A1* | 5/2012 | Dai | H04N 5/378 348/308 |
| 2012/0138807 A1 | 6/2012 | Kondou | |
| 2013/0120619 A1* | 5/2013 | Mo | H04N 5/378 348/243 |
| 2013/0140434 A1* | 6/2013 | Yamazaki | H01L 27/146 250/208.1 |
| 2013/0153750 A1* | 6/2013 | Arii | H04N 5/3597 250/208.1 |
| 2014/0184865 A1* | 7/2014 | Muto | H03M 1/183 348/300 |
| 2014/0263966 A1* | 9/2014 | Hikosaka | H04N 5/3745 250/208.1 |
| 2015/0109506 A1* | 4/2015 | Aibara | H04N 5/37455 348/308 |
| 2015/0124138 A1* | 5/2015 | Ueda | H04N 5/3575 348/308 |

FOREIGN PATENT DOCUMENTS

| | | |
|---|---|---|
| EP | 2 950 524 A1 | 12/2015 |
| JP | H04-196688 A | 7/1992 |
| JP | 2009-272909 A | 11/2009 |
| JP | 2010-147948 A | 7/2010 |
| JP | 2011-109584 A | 6/2011 |
| JP | 2012-235193 A | 11/2012 |

OTHER PUBLICATIONS

Japanese Office Action dated Sep. 29, 2015 issued in JP 2015-534870.
Japanese Office Action dated Nov. 30, 2015 issued in JP 2015-534870.
Extended Supplementary European Search Report dated Jan. 23, 2018 in European Patent Application No. 15 81 4044.2.
Chinese Office Action dated Feb. 2, 2018 in Chinese Patent Application No. 201580002235.7.

* cited by examiner

007
IMAGE SENSOR, IMAGING DEVICE, ENDOSCOPE, AND ENDOSCOPE SYSTEM

CROSS-REFERENCE TO RELATED APPLICATIONS

This application is a continuation of PCT international application Ser. No. PCT/JP2015/056678 filed on Mar. 6, 2015 which designates the United States, incorporated herein by reference, and which claims the benefit of priority from Japanese Patent Application No. 2014-137103, filed on Jul. 2, 2014, incorporated herein by reference.

BACKGROUND

1. Technical Field

The disclosure relates to an image sensor, an imaging device, an endoscope, and an endoscope system that are configured to image a subject to generate image data of the subject.

2. Related Art

Conventionally, it is known that a plurality of light-shielded pixels called optical black (OB) pixels is provided to obtain a black reference level in an imaging device including an image sensor such as a charge coupled device (CCD) and a complementary metal oxide semiconductor (CMOS) (for example, see JP 2012-235193 A). In this technique, OB pixels are provided over a plurality of rows and a plurality of columns, and a black reference signal which determines a black level in an OB region is subtracted from an imaging signal in an effective region which is not light-shielded. By doing so, a noise component included in the imaging signal in the effective region is eliminated.

SUMMARY

In some embodiments, an image sensor includes: a reference signal generation unit configured to generate and output a reference signal in accordance with a predetermined voltage; a plurality of pixels disposed in a two-dimensional matrix form and configured to receive light from outside, and to generate and output an imaging signal in accordance with an amount of the received light; a transfer unit configured to transfer the reference signal output from the reference signal generation unit and the imaging signal output from each of the plurality of pixels, during different periods; and an output unit configured to separately hold the reference signal and the imaging signal transferred from the transfer unit, sequentially switch between the reference signal and the imaging signal to output the switched signal.

In some embodiments, an imaging device includes the image sensor.

In some embodiments, an endoscope includes the imaging device at a distal end side of an insertion unit of the endoscope.

In some embodiments, an endoscope system includes the endoscope and a processing device configured to convert an imaging signal to an image signal.

The above and other features, advantages and technical and industrial significance of this invention will be better understood by reading the following detailed description of presently preferred embodiments of the invention, when considered in connection with the accompanying drawings.

DETAILED DESCRIPTION

As modes for carrying out the invention (hereinafter referred to as "embodiment(s)"), an endoscope system having an imaging device will be described below. The present invention is not limited by the embodiments. The same reference signs are used to designate the same elements throughout the drawings. The drawings are schematic, and a relationship between the thickness and the width of each member, and a ratio among each member therein are different from those in reality. There may be a difference in dimensions and ratios of corresponding members among the drawings.

First Embodiment

Configuration of Endoscope System

Figure 1:
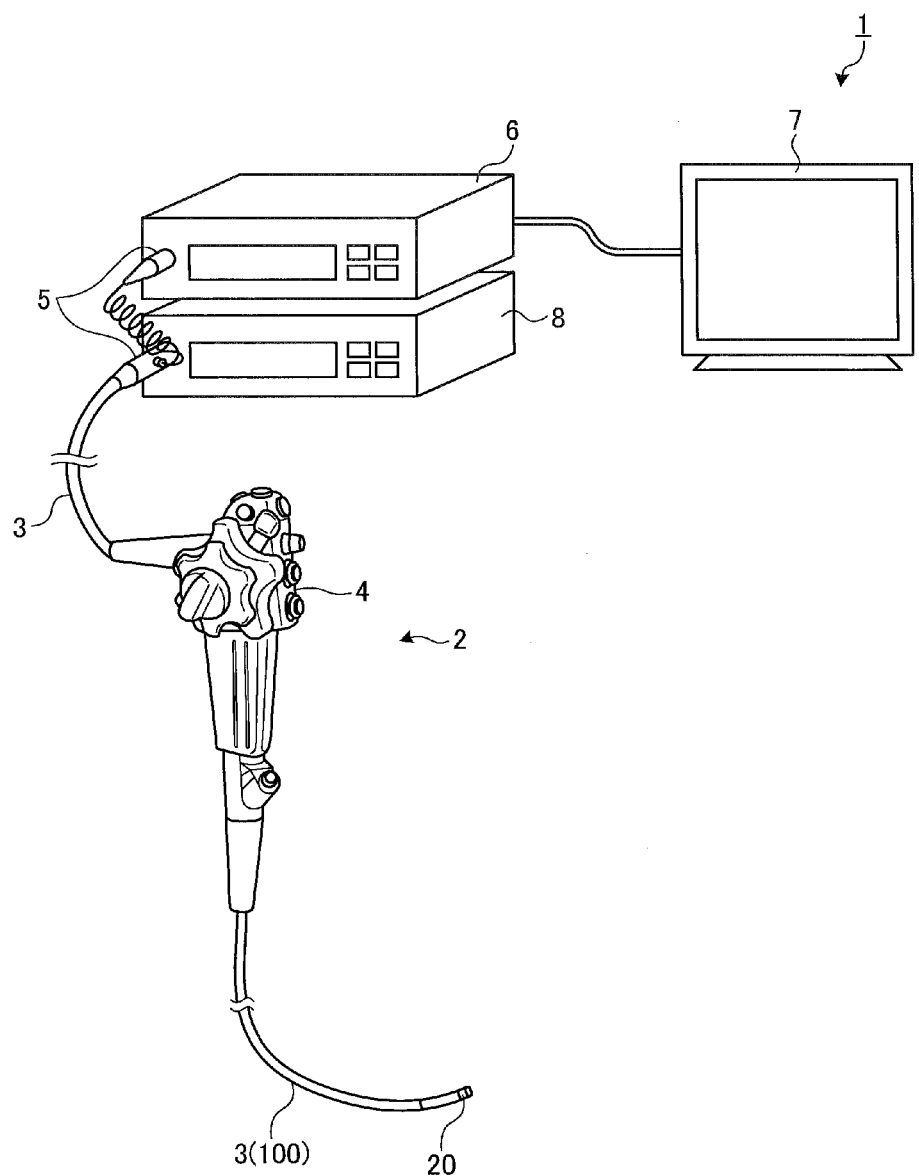
FIG. 1 is a schematic view illustrating an overall configuration of an endoscope system according to a first embodiment of the present invention.

FIG. 1 is a schematic view illustrating an overall configuration of an endoscope system according to a first embodiment of the present invention. An endoscope system 1 illustrated in FIG. 1 includes an endoscope 2, a transmission cable 3, a connector unit 5, a processor 6 (processing device), a display device 7, and a light source device 8.

The endoscope 2 captures an in-vivo image of a subject by inserting an insertion unit 100, which is a part of the transmission cable 3, into a body cavity of the subject, and outputs an imaging signal (image data) to the processor 6.

The transmission cable 3 connects the endoscope 2 and the connector unit 5, and connects the endoscope 2 and the light source device 8.

The connector unit 5 is connected to the endoscope 2, the processor 6, and the light source device 8. The connector unit 5 performs predetermined signal processing for the imaging signal output from the endoscope 2 connected thereto, and performs analog-digital conversion (A/D conversion) of the imaging signal to output the converted signal as an image signal to the processor 6.

The processor 6 performs predetermined image processing for the image signal output from the connector unit 5, and collectively controls the entire endoscope system 1. In the first embodiment, the processor 6 functions as a processing device.

The display device 7 displays an image corresponding to the image signal for which the processor 6 has performed the image processing. In addition, the display device 7 displays a variety of information regarding the endoscope system 1.

The light source device 8 includes, for example, a halogen lamp or white light emitting diode (LED), and irradiates a subject with illumination light emitted from a distal end side of the insertion unit of the endoscope 2 through the connector unit 5 and the transmission cable 3.

In the endoscope 2, on a side of one end of the transmission cable 3, which is the side of a distal end 101 of the insertion unit 100 inserted into a body cavity of the subject, an imaging unit 20 (imaging device) which captures an in-vivo image is provided. To a side of a proximal end 102 of the insertion unit 100, an operating unit 4 which receives various operations for the endoscope 2 is connected. With the transmission cable 3, the imaging unit 20 is connected to the connector unit 5 through the operating unit 4. An imaging signal of an image captured by the imaging unit 20 is output to the connector unit 5, for example, through the transmission cable 3 having a length of several meters.

Figure 2:
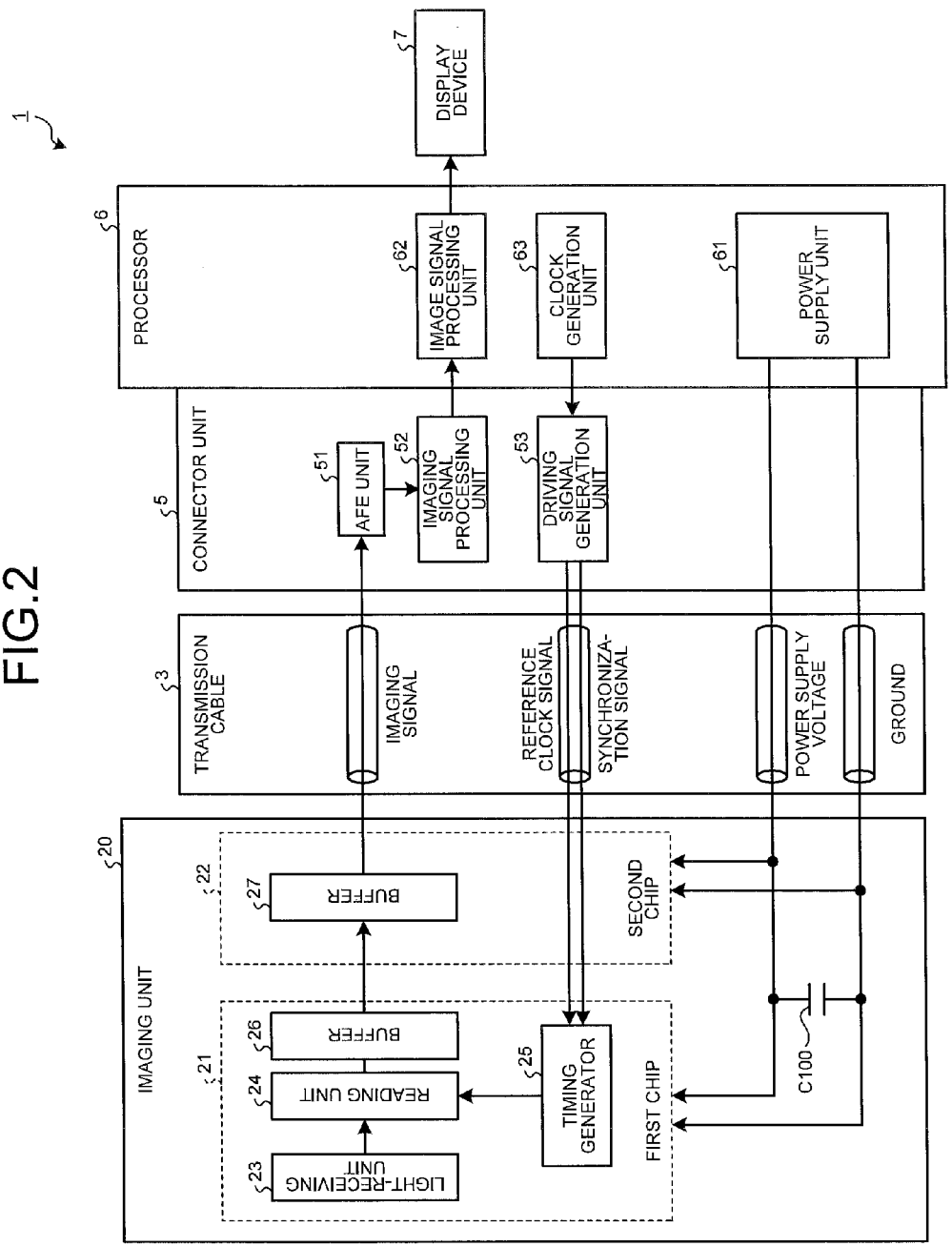
FIG. 2 is a block diagram illustrating functions of major parts of the endoscope system according to the first embodiment of the present invention.

FIG. 2 is a block diagram illustrating functions of major parts of the endoscope system 1. With reference to FIG. 2, a detailed configuration of each unit of the endoscope system 1 and electric signal pathways in the endoscope system 1 are described.

As illustrated in FIG. 2, the imaging unit 20 includes a first chip (image sensor) 21 having a light-receiving unit 23, a reading unit 24, a timing generator 25 and a buffer 26, and a second chip 22 having a buffer 27.

The first chip 21 of the imaging unit 20 includes the light-receiving unit 23, the reading unit 24, the timing generator 25, and the buffer 26. In the light-receiving unit 23, a plurality of unit pixels is disposed in a two-dimensional matrix form in a matrix direction. The reading unit 24 reads an imaging signal photoelectrically converted in the light-receiving unit 23. The timing generator 25 generates a timing signal based on a reference clock signal and a synchronization signal input from the connector unit 5 and outputs the timing signal to the reading unit 24. The buffer 26 temporarily holds the imaging signal which the reading unit 24 has read from the light-receiving unit 23 and a reference signal. A more detailed configuration of the first chip 21 will be described later with reference to FIG. 3.

The second chip 22 of the imaging unit 20 includes the buffer 27. The buffer 27 functions as a transmission unit which transmits, to the processor 6 through the transmission cable 3 and the connector unit 5, only an alternating-current component of the imaging signal output from the first chip 21. Combination of circuits mounted on the first chip 21 and the second chip 22 can be appropriately changed in accordance with the convenience of setting.

The imaging unit 20 receives a power supply voltage (VDD) generated in a power supply unit 61 in the processor 6, together with a ground (GND), through the transmission cable 3. A capacitor C100 for stabilizing power supply is provided between the power supply voltage (VDD) and the ground (GND) supplied to the imaging unit 20.

The connector unit 5 includes an analog front end unit 51 (hereinafter referred to as "AFE unit 51"), an imaging signal processing unit 52, and a driving signal generation unit 53. The connector unit 5 electrically connects the endoscope 2 (imaging unit 20) and the processor 6, and functions as a relay processing unit which relays an electric signal. The connector unit 5 and the imaging unit 20 are connected to each other through the transmission cable 3, and the connector unit 5 and the processor 6 are connected to each other through a coiled cable. The connector unit 5 is also connected to the light source device 8.

The AFE unit 51 receives an imaging signal transmitted from the imaging unit 20, performs impedance matching with a passive device such as a resistor, then extracts an alternating-current component by a capacitor, and determines an operating point with a voltage dividing resistor. The AFE unit 51 performs A/D conversion of the analog imaging signal transmitted from the imaging unit 20, and outputs the converted signal as a digital imaging signal to the imaging signal processing unit 52.

The imaging signal processing unit 52 performs predetermined signal processing such as elimination of vertical lines and elimination of noise for the digital imaging signal input from the AFE unit 51, and outputs the digital imaging signal which has been subjected to the processing to the processor 6. The imaging signal processing unit 52 includes, for example, a field programmable gate array (FPGA).

The driving signal generation unit 53 generates a synchronization signal which indicates a starting position of each frame based on a reference clock signal (for example, a 27-MHz clock signal). The reference clock signal is supplied from the processor 6 and serving as a reference of operation of each element of the endoscope 2. The driving signal generation unit 53 outputs the synchronization signal, together with the reference clock signal, to the timing generator 25 of the imaging unit 20 through the transmission cable 3. Here, the synchronization signal generated by the driving signal generation unit 53 includes a horizontal synchronization signal and a vertical synchronization signal.

The processor 6 is a control device which collectively controls the entire endoscope system 1. The processor 6 includes the power supply unit 61, an image signal processing unit 62, and a clock generation unit 63.

The power supply unit 61 generates a power supply voltage (VDD), and supplies the generated power supply voltage, together with a ground (GND), to the imaging unit 20 through the connector unit 5 and the transmission cable 3.

The image signal processing unit 62 performs image processing for the digital imaging signal which has been subjected to the signal processing in the imaging signal processing unit 52, and converts the digital imaging signal to an image signal. Examples of the image processing include synchronization processing, white balance (WB) adjustment processing, gain adjustment processing, gamma correction processing, digital-analog (D/A) conversion processing, and format conversion processing. Then, the image signal processing unit 62 outputs the image signal to the display device 7.

The clock generation unit 63 generates a reference clock signal serving as a reference of operation of each element of the endoscope system 1, and outputs the reference clock signal to the driving signal generation unit 53.

The display device 7 displays an image captured by the imaging unit 20 based on an image signal input from the image signal processing unit 62. The display device 7 includes a display panel employing liquid crystal, organic electroluminescence (EL), or the like.

Configuration of First Chip

Next, the detailed configuration of the above-described first chip 21 will be described.

Figure 3:
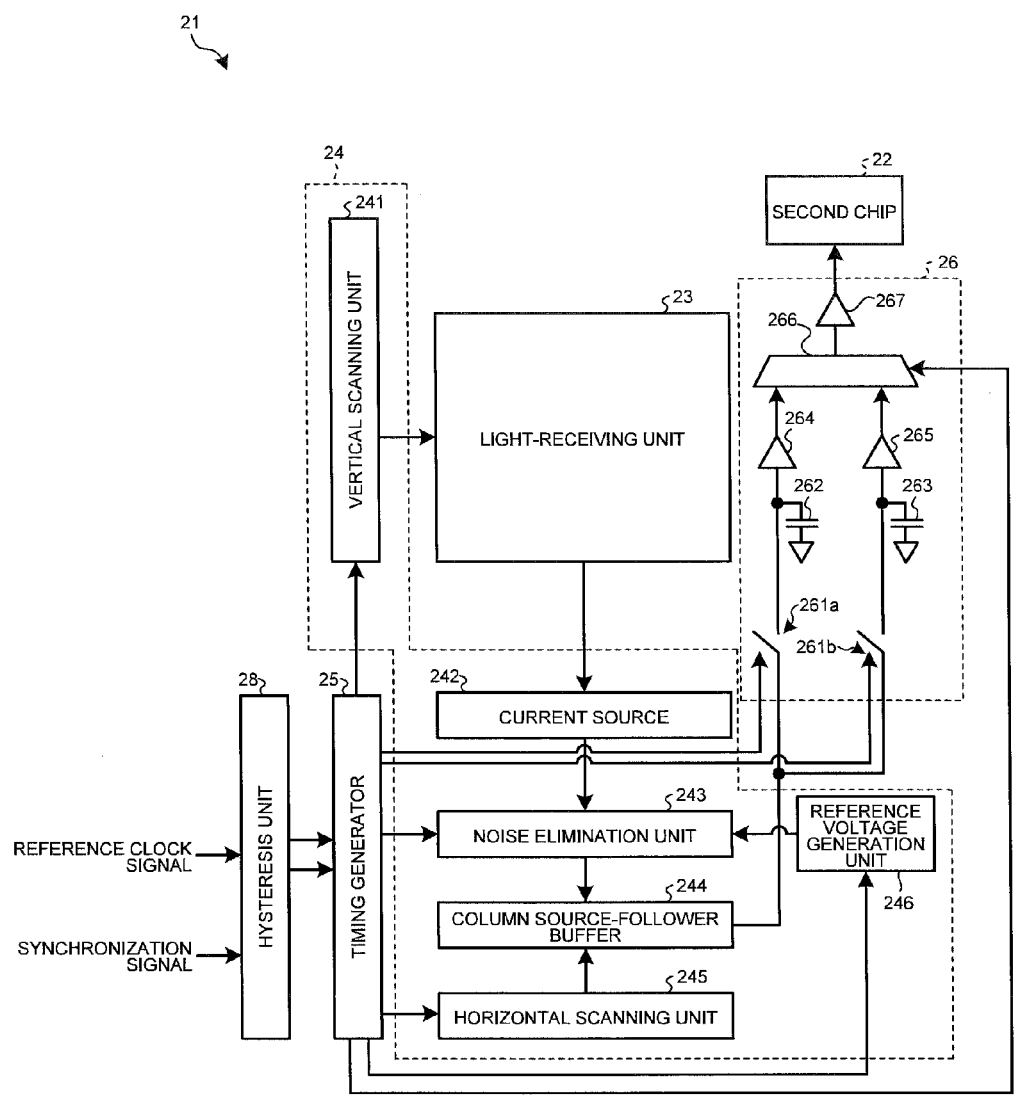
FIG. 3 is a block diagram illustrating a detailed configuration of a first chip illustrated in FIG. 2.
Figure 4:
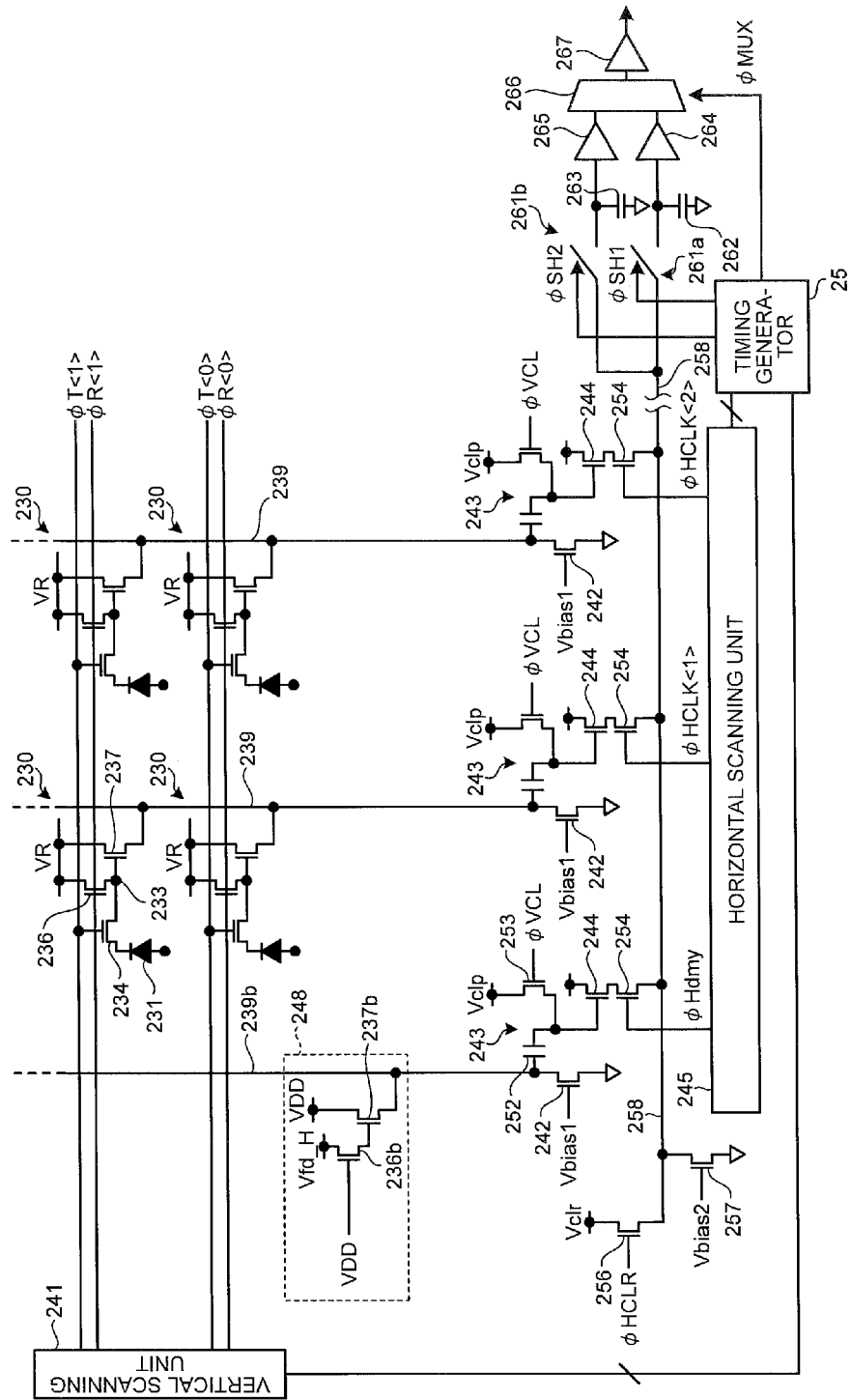
FIG. 4 is a circuit diagram illustrating a configuration of the first chip illustrated in FIG. 2.

FIG. 3 is a block diagram illustrating the detailed configuration of the first chip 21 illustrated in FIG. 2. FIG. 4 is a circuit diagram illustrating the configuration of the first chip 21.

As illustrated in FIGS. 3 and 4, the first chip 21 includes the light-receiving unit 23, the reading unit 24 (driving unit), the timing generator 25, the buffer 26, and a hysteresis unit 28.

The hysteresis unit 28 shapes waveforms of the reference clock signal and the synchronization signal input through the transmission cable 3, and outputs, to the timing generator 25, the reference clock signal and the synchronization signal of which the waveforms have been shaped.

The timing generator 25 generates various driving signals based on the reference clock signal and the synchronization signal input from the hysteresis unit 28, and outputs the driving signals to a vertical scanning unit 241, a noise elimination unit 243, a horizontal scanning unit 245, and a reference voltage generation unit 246 of the reading unit 24 described later, a first switch 261a, a second switch 261b, and a multiplexer 266 of the buffer 26 described later.

The reading unit 24 transfers, during periods different from each other, an imaging signal output from each of a plurality of pixels in the light-receiving unit 23 described later, and a reference signal output from a reference signal generation unit. In the first embodiment, the reading unit 24 functions as a transfer unit.

Here, the detailed configuration of the reading unit 24 will be described. The reading unit 24 includes the vertical scanning unit 241 (row selection circuit), a current source 242, the noise elimination unit 243, a column source-follower buffer 244 (transistor), the horizontal scanning unit 245 (column selection circuit), the reference voltage generation unit 246, and a reference signal generation unit 248.

Based on the driving signal (such as φT and φR) input from the timing generator 25, the vertical scanning unit 241 applies row selection pulses φT<M> and φR<M> to a selected row <M> (M=0, 1, 2, . . . , m−1, m) of the light-receiving unit 23, drives each unit pixel 230 of the light-receiving unit 23 with the current source 242, transfers to a vertical transfer line (first transfer line) 239 and outputs to the noise elimination unit 243, an imaging signal and a noise signal at the time of pixel resetting.

The noise elimination unit 243 eliminates output variation for each unit pixel 230 and the noise signal at the time of pixel resetting, and outputs an imaging signal photoelectrically converted in each unit pixel 230. Details of the noise elimination unit 243 will be described later.

Based on the driving signal (φHCLK) supplied from the timing generator 25, the horizontal scanning unit 245 applies a column selection pulse φHCLK<N> to a selected column <N> (N=0, 1, 2, . . . , n−1, n) of the light-receiving unit 23, transfers to a horizontal transfer line (second transfer line) 258 through the noise elimination unit 243 and outputs to an output unit 267, an imaging signal photoelectrically converted in each unit pixel 230.

In the light-receiving unit 23 of the first chip 21, a number of unit pixels 230 (photoelectric converter) are disposed in a two-dimensional matrix form. Each of the unit pixels 230 includes a photoelectric conversion element 231 (photodiode), a charge converter 233, a transfer transistor 234 (first transfer unit), a pixel resetting unit 236 (transistor), a pixel source-follower transistor 237, and the reference signal generation unit 248. In this description, one or a plurality of photoelectric conversion elements, and a transfer transistor which transfers a signal charge from each of the photoelectric conversion elements to the charge converter 233 are referred to as a unit cell. In other words, the unit cell includes a set of one or a plurality of photoelectric conversion elements and the transfer transistor, and each of the unit pixels 230 includes one unit cell.

The photoelectric conversion element 231 photoelectrically converts incident light to a signal charge in an amount corresponding to the amount of the incident light, and accumulates the signal charge. A cathode side of the photoelectric conversion element 231 is connected to one end side of the transfer transistor 234, and an anode side thereof is connected to the ground GND.

The charge converter 233 is formed of a floating diffusion capacitor (FD), and converts the charge accumulated in the photoelectric conversion element 231 into voltages.

The transfer transistor 234 transfers the charge to the charge converter 233 from the photoelectric conversion element 231. To a gate of the transfer transistor 234, a signal line through which a driving signal φT is supplied is connected, and the other end side thereof is connected to the charge converter 233. When the driving signal φT is supplied from the vertical scanning unit 241 through the signal line, the transfer transistor 234 is turned to an ON state, and a signal charge is transferred from the photoelectric conversion element 231 to the charge converter 233.

The pixel resetting unit 236 (transistor) resets the charge converter 233 to a predetermined potential. In the pixel resetting unit 236, one end side thereof is connected to a variable voltage VR, another end side thereof is connected to the charge converter 233, and to a gate thereof, a signal line through which a driving signal φR is supplied is connected. When the driving signal φR is supplied from the vertical scanning unit 241 through the signal line, the pixel resetting unit 236 is turned to an ON state, and a signal charge accumulated in the charge converter 233 is released to reset the charge converter 233 to a predetermined potential.

In the pixel source-follower transistor 237 (pixel amplifying unit), one end side thereof is connected to the variable voltage VR, and another end side thereof is connected to a vertical transfer line 239. To a gate thereof, a signal subjected to voltage conversion in the charge converter 233 (imaging signal or signal upon resetting) is input. When the driving signal φT is supplied to the gate of the transfer transistor 234 after the selection operation described later, a charge is read from the photoelectric conversion element 231, subjected to voltage conversion in the charge converter 233, and then transferred to the vertical transfer line 239 through the pixel source-follower transistor 237.

In the first embodiment, in a case where the driving signal φR is supplied to the gate of the pixel resetting unit 236 when the variable voltage VR is at a level of the power supply voltage VDD (for example, 3.3 V), the pixel source-follower transistor 237 is turned to an ON state, and a unit pixel including the pixel resetting unit 236 is selected (selection operation). In addition, in a case where the driving signal φR is supplied to the gate of the pixel resetting unit 236 when the variable voltage VR is at a level of deselection voltage Vfd_L (for example, 1 V), the pixel source-follower transistor 237 is turned to an OFF state, and the unit pixel including the pixel resetting unit 236 is deselected (deselection operation).

The reference signal generation unit 248 is connected to a dedicated vertical transfer line 239b, independently from the columns of the unit pixels 230. The reference signal generation unit 248 generates a reference signal according to a predetermined voltage, and outputs the signal.

Here, the detailed configuration of the reference signal generation unit 248 will be described. The reference signal generation unit 248 includes a resetting unit for reference signal generation 236b (transistor), a source-follower transistor for reference signal generation 237b. In other words, it is a configuration obtained by omitting the photoelectric conversion element 231 (photodiode), the charge converter 233, and the transfer transistor 234 (first transfer unit) from the unit pixel 230.

The resetting unit for reference signal generation 236b fixes a gate of the source-follower transistor for reference signal generation 237b to a predetermined potential. In the resetting unit for reference signal generation 236b, one end side thereof is connected to a voltage for reference signal Vfd_H supplied from the reference voltage generation unit 246, another end side thereof is connected to the gate of the source-follower transistor for reference signal generation 237b, and to the gate thereof, a signal line through which a power supply voltage VDD is supplied is connected. Since the signal line through which the power supply voltage VDD is supplied is connected to the gate of the resetting unit for reference signal generation 236b, the resetting unit for reference signal generation 236b consistently fixes the gate of the source-follower transistor for reference signal generation 237b to the voltage Vfd_H.

In the source-follower transistor for reference signal generation 237b, one end side thereof is connected to the power supply voltage VDD, and another end side thereof is connected to the vertical transfer line 239b. To a gate thereof, a voltage for a reference signal Vfd_H is input. A reference signal in accordance with the voltage for a reference signal Vfd_H (black reference signal) is consistently transferred to the vertical transfer line 239b through the source-follower transistor for reference signal generation 237b.

The dedicated vertical transfer line 239b for the reference signal generation unit 248 is the same as the normal vertical transfer line 239 except that the reference signal generation unit 248 is connected thereto instead of a plurality of rows of the unit pixels 230. In other words, the black reference signal transferred by the vertical transfer line 239b is input to the noise elimination unit 243 in the same manner as for the imaging signal transferred by the vertical transfer line 239.

In the current source 242, one end side thereof is connected to the vertical transfer line 239, another end side thereof is connected to the ground GND, and to a gate thereof, a bias voltage Vbias1 is applied. The unit pixel 230 and the reference signal generation unit 248 are driven by the current source 242, and an output of the unit pixel 230 (imaging signal) and an output of the reference signal generation unit 248 (black reference signal) are read to the vertical transfer line 239. The signals read to the vertical transfer line 239 (imaging signal and black reference signal) are input to the noise elimination unit 243.

The noise elimination unit 243 includes a transfer capacitor 252 (AC-coupling capacitor) and a clamp switch 253 (transistor). In the transfer capacitor 252, one end side thereof is connected to the vertical transfer line 239, and another end side thereof is connected to the column source-follower buffer 244. In the clamp switch 253, one end side thereof is connected to a signal line through which a clamp voltage Vclp is supplied from the reference voltage generation unit 246. Another end side of the clamp switch 253 is connected to a portion between the transfer capacitor 252 and the column source-follower buffer 244, and to a gate thereof, a driving signal φVCL is input from the timing generator 25. An imaging signal input to the noise elimination unit 243 includes a noise component.

When the driving signal φVCL is input to the gate of the clamp switch 253 from the timing generator 25, the clamp switch 253 is turned to an ON state. In accordance therewith, the transfer capacitor 252 is reset by the clamp voltage Vclp supplied from the reference voltage generation unit 246. The black reference signal and the imaging signal of which the noise has been eliminated in the noise elimination unit 243 are input to a gate of the column source-follower buffer 244.

Since the noise elimination unit 243 does not need a capacitor for sampling (sampling capacitor), a capacitance of the transfer capacitor 252 (AC-coupling capacitor) only needs to be a capacitance which is sufficient for the input capacitance of the column source-follower buffer 244. In addition, since there is no sampling capacitor, an area occupied by the noise elimination unit 243 in the first chip 21 can be reduced.

In the column source-follower buffer 244, one end side thereof is connected to the power supply voltage VDD, another end side thereof is connected to one end side of a column selection switch 254 (second transfer unit), and to a gate thereof, the imaging signal and the black reference signal are input through the noise elimination unit 243. In the column selection switch 254, one end side thereof is connected to another end side of the column source-follower buffer 244, and another end side thereof is connected to a horizontal transfer line 258 (second transfer line).

In a horizontal resetting transistor 256, one end side thereof is connected to a horizontal resetting voltage Vclr, and another end side thereof is connected to the horizontal transfer line 258. To a gate of the horizontal resetting transistor 256, a driving signal φHCLR is input from the timing generator 25. When the driving signal φHCLR is input to the gate of the horizontal resetting transistor 256 from the timing generator 25, the horizontal resetting transistor 256 is turned to an ON state, and the horizontal transfer line 258 is reset.

In the column selection switch 254, one end side thereof is connected to another end side of the column source-follower buffer 244, and another end side thereof is connected to the horizontal transfer line (second transfer line) 258. To a gate of the column selection switch 254, a signal line through which a driving signal (column selection pulse) φHCLK<N> is supplied from the horizontal scanning unit 245 is connected. When the driving signal φHCLK<N> is supplied to the gate of the column selection switch 254 of a column <N> from the horizontal scanning unit 245, the column selection switch 254 is turned to an ON state, and signals of the vertical transfer line 239 of the column <N> (imaging signal and black reference signal) are transferred to the horizontal transfer line 258.

In a constant current source 257, one end side thereof is connected to the horizontal transfer line 258, another end side thereof is connected to the ground GND, and to a gate thereof, a bias voltage Vbias2 is applied. The constant current source 257 drives the column source-follower buffer 244, and reads the imaging signal and the black reference signal from the vertical transfer line 239 and the vertical transfer line 239b, respectively, to the horizontal transfer line 258. The signals read to the horizontal transfer line 258 are input to the buffer 26 and held therein.

The reference voltage generation unit 246 generates, based on the signal input from the timing generator 25, the voltage for a reference signal Vfd_H from the power supply voltage VDD and the clamp voltage Vclp of the noise elimination unit 243. A configuration of the reference voltage generation unit 246 will be described in detail with FIGS. 5A and 5B described later.

The buffer 26 separately holds the imaging signal and the reference signal (black reference signal) input from the horizontal transfer line 258, sequentially switches, based on the signals input from the timing generator 25, between the imaging signal and the reference signal (black reference signal), and outputs the switched signals to the second chip 22. In the first embodiment, the buffer 26 functions as an output unit.

Here, the detailed configuration of the buffer 26 will be described. The buffer 26 includes the first switch 261a, the second switch 261b, a first holding unit 262, a second holding unit 263, a first operational amplifier 264, a second operational amplifier 265, the multiplexer 266, and the output unit 267.

In the first switch 261a, one end side thereof is connected to the horizontal transfer line 258 and another end side thereof is connected to an input of the first operational amplifier 264. The first switch 261a connects, based on a driving signal (φSH1) input from the timing generator 25, the first holding unit 262 and the horizontal transfer line 258.

In the second switch 261b, one end side thereof is connected to the horizontal transfer line 258 and another end side thereof is connected to an input of the second operational amplifier 265. The second switch 261b connects, based on a driving signal (φSH2) input from the timing generator 25, the second holding unit 263 and the horizontal transfer line 258.

The first holding unit 262 includes a capacitor, and one end side thereof is connected to another end side of the first switch 261a and the input of the first operational amplifier 264, and another end side thereof is connected to the ground. An output of the first operational amplifier 264 is connected to an input of the multiplexer 266. The first holding unit 262 holds the reference signal (black reference signal) input through the horizontal transfer line 258, and while the first switch 261a is in an OFF state, outputs the held reference signal (black reference signal) to the multiplexer 266. Here, "to hold the reference signal (black reference signal)" means "to hold an amount of charge corresponding to a signal level (voltage) of the reference signal". In addition, it is more preferable when a capacitance C1 of the first holding unit 262 is larger than a capacitance C2 of the second holding unit 263 (C1>C2).

The second holding unit 263 includes a capacitor, and one end side thereof is connected to another end side of the second switch 261b and the input of the second operational amplifier 265, and another end side thereof is connected to the ground. An output of the second operational amplifier 265 is connected to the input of the multiplexer 266. The second holding unit 263 holds the imaging signal input through the horizontal transfer line 258, and while the second switch 261b is in an OFF state, outputs the held imaging signal to the multiplexer 266. Here, "to hold the imaging signal" means "to hold an amount of charge corresponding to the imaging signal".

The multiplexer 266 is driven by a driving signal (φMUXSEL) supplied from the timing generator 25, sequentially switches between the reference signal (black reference signal) input from the first holding unit 262 and the imaging signal input from the second holding unit 263, and outputs the switched signals to the second chip 22 through the output unit 267 (amplifier). In that sense, the multiplexer 266 functions as a switching unit in the first embodiment. When a pulsed driving signal (φMUXSEL: High) is output from the timing generator 25, the multiplexer 266 outputs the imaging signal input from the second holding unit 263 to the second chip 22.

The output unit 267 performs, if necessary, signal amplification on the imaging signal whose noise has been eliminated and a reference voltage Vref, and outputs the imaging signal and the reference voltage alternately to the second chip 22.

The second chip 22 transmits only an alternating-current component of the imaging signal whose noise has been eliminated and the reference voltage Vref, to the connector unit 5 through the transmission cable 3.

Configuration of Reference Voltage Generation Unit

Figure 5A:
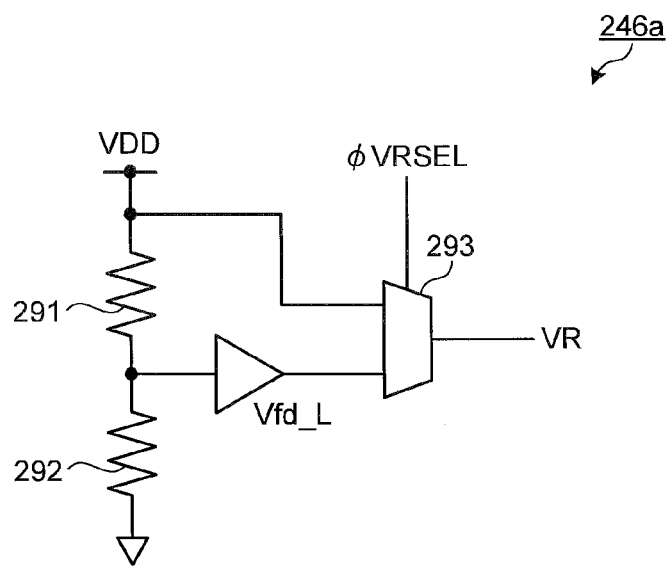
FIG. 5A is a circuit diagram illustrating a configuration of a reference voltage generation unit of a reading unit of the endoscope system according to the first embodiment of the present invention.
Figure 5B:
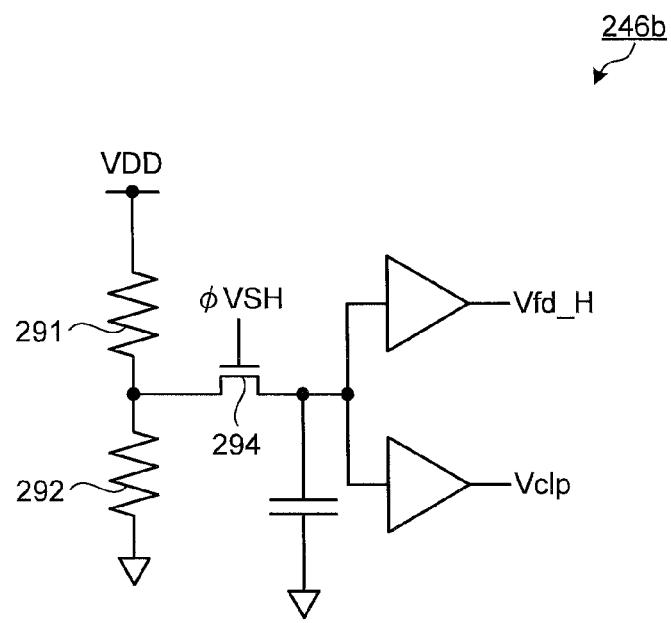
FIG. 5B is a circuit diagram illustrating a configuration of a reference voltage generation unit of the reading unit of the endoscope system according to the first embodiment of the present invention.

Next, the configuration of the reference voltage generation unit 246 will be described. FIGS. 5A and 5B are circuit diagrams illustrating the configuration of the reference voltage generation unit 246.

A reference voltage generation unit 246a illustrated in FIG. 5A includes a resistance voltage divider circuit including two resistors 291 and 292, and a multiplexer 293 driven by a driving signal φVRSEL.

In accordance with the driving signal φVRSEL input from the timing generator 25, the multiplexer 293 alternately switches between the power supply voltage VDD and the deselection voltage Vfd_L generated in the resistance voltage divider circuit, and applies the switched voltages as the variable voltage VR to all pixels and the reference signal generation unit 248.

A reference voltage generation unit 246b illustrated in FIG. 5B includes a resistance voltage divider circuit including two resistors 291 and 292, and a switch 294 (transistor) driven by a driving signal φVSH. The reference voltage generation unit 246b generates, at the timing when the driving signal φVSH is driven by the driving of the switch 294, the voltage for a reference signal Vfd_H and the clamp voltage Vclp of the noise elimination unit 243 from the power supply voltage VDD.

Operation of Imaging Unit 20

Next, a drive timing of the imaging unit 20 will be described.

Figure 6:
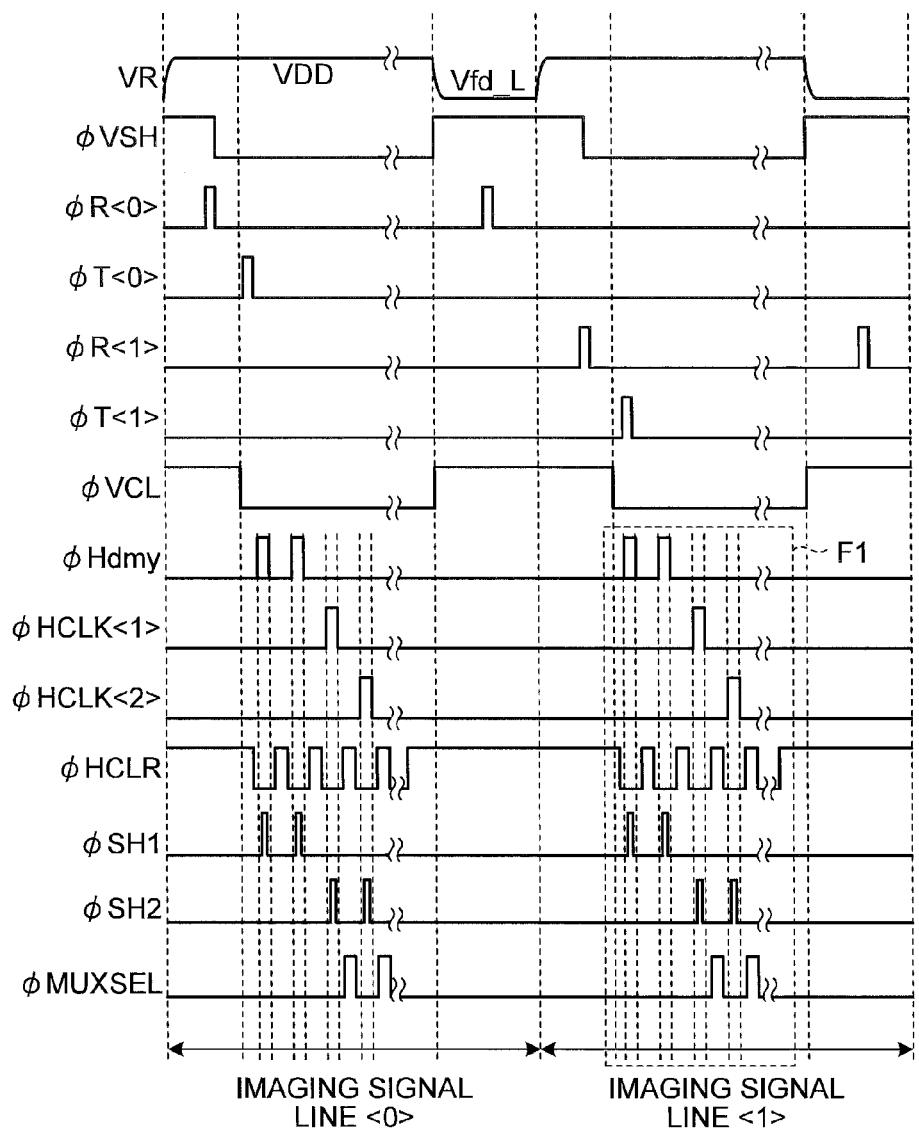
FIG. 6 is a timing chart illustrating a drive timing of an imaging unit according to the first embodiment of the present invention.
Figure 7:
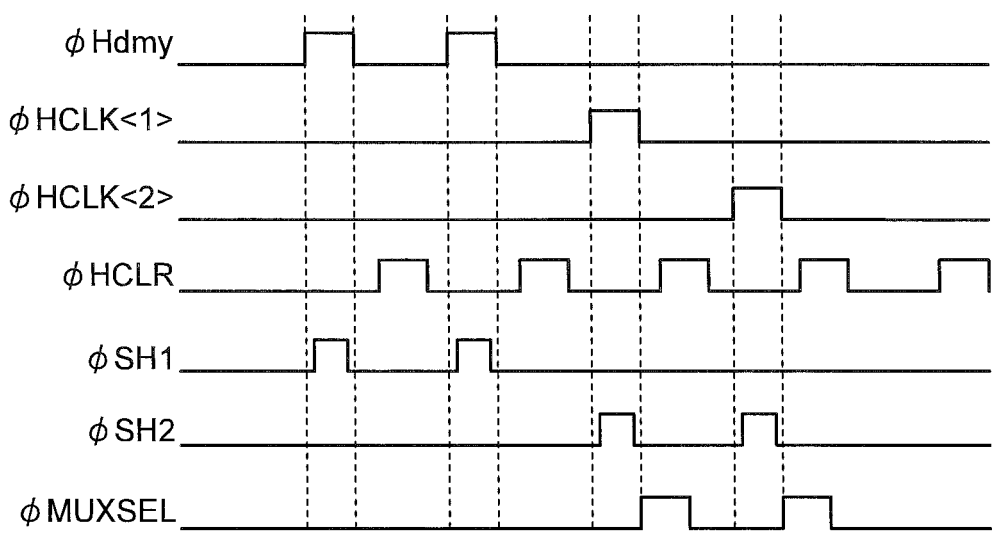
FIG. 7 is a timing chart illustrating an enlarged region of FIG. 6.

FIG. 6 is a timing chart illustrating the drive timing of the imaging unit 20. FIG. 7 is a timing chart illustrating an enlarged region F1 of FIG. 6. In FIGS. 6 and 7, the variable voltage VR, the driving signal φVSH, and driving signals φR, φT, φVCL, φHdmy, φHCLK, φHCLR, φSH1, φSH2, and φMUXSEL are illustrated sequentially from the top. In FIGS. 6 and 7, the driving signals φR and φT are signals in cases where the row <M> is <0> and <1>, and the driving signal φHCLK is a signal in cases where the column <N> is <1> and <2>.

As illustrated in FIGS. 6 and 7, first, the variable voltage VR is adjusted to be a VDD level (for example, 3.3 V). Next, while keeping the variable voltage VR at the VDD level, a driving signal φR<0> is applied in a pulsed manner to a gate of the pixel resetting unit 236 of a pixel row <0>. Consequently, the power supply voltage VDD is applied to a gate of the pixel source-follower transistor 237 of the pixel row <0>, and the pixel source-follower transistor 237 is turned to an ON state. Through the above processes, the unit pixel 230 included in the pixel row <0> is selected (selection operation).

At the same time, a noise signal is output to the vertical transfer line 239 from the unit pixel 230. The noise signal includes fluctuations unique to the unit pixel 230 to be read, a noise upon pixel resetting, and the like. At that time, a voltage of a gate of the column source-follower buffer 244 is adjusted to be the clamp voltage Vclp by making a transition of the clamp switch 253 from an ON state (φVCL: High) to an OFF state (φVCL: Low). The clamp voltage Vclp is determined at a falling timing of φVSH.

Next, by turning the transfer transistor 234 to an ON state (φT<0>: High) in a pulsed manner, a signal, which is obtained by converting, by the charge converter 233, the charge photoelectrically converted by the photoelectric conversion element 231, is read to the vertical transfer line 239. Through this operation, an imaging signal (optical signal) obtained by subtracting the noise signal is output to the gate of the column source-follower buffer 244 through the transfer capacitor 252. Here, the signal output to the gate of the column source-follower buffer 244 is a signal sampled based on the clamp voltage Vclp as a reference.

After sampling a black reference signal based on the clamp voltage Vclp as a reference, the horizontal resetting transistor 256 is turned to an OFF state (φHCLR: Low) to cancel the resetting of the horizontal transfer line 258, and the column selection switch 254 provided on the most downstream side of a vertical transfer line 239a is turned to an ON state (φHdmy: High). By doing so, the black reference signal is transferred to the horizontal transfer line 258. Thereafter, by turning the first switch 261a to an ON state (φSH1: High), the reference signal (black reference signal) is sampled by the first holding unit 262 and held therein. Subsequently, the first switch 261a is turned to an OFF state (φSH1: Low), and the column selection switch 254 at the most downstream side is turned to an OFF state (φHdmy: Low). A period during which the first switch 261a is in the ON state (sampling period) is shorter than a period during which the column selection switch 254 at the most downstream side is in the ON state (transfer period).

Thereafter, the horizontal resetting transistor 256 is turned to an ON state (φHCLR: High) in a pulsed manner to reset the horizontal transfer line 258 again. During the above operation, a driving signal is not output to the multiplexer 266 (φMUXSEL: Low). Therefore, the multiplexer 266 outputs the reference signal (black reference signal) held by the first holding unit 262 to the output unit 267.

In the first embodiment, a series of operations performed after the transfer transistor 234 has been turned to the ON state (φT<0>: High) in a pulsed manner, in other words, a series of operations including from the operation for turning the horizontal resetting transistor 256 to the OFF state (φHCLR: Low) to the operation for outputting the reference signal (black reference signal) to the output unit 267, is repeated a predetermined number of times (in FIGS. 6 and 7, twice). In the first embodiment, the reference signal (black reference signal) is sampled by the first holding unit 262 and held therein. Therefore, charging is required only for a relatively small capacitance in the first chip 21. Accordingly, the number of times of repeating the series of operations can be reduced to, approximately, two to ten.

Next, by turning the column selection switch 254 of the column <1> to an ON state (φHCLK<1>: High), an imaging signal of the column <1> is transferred to the horizontal transfer line 258. Thereafter, by turning the second switch 261b to an ON state (φSH2: High), the imaging signal is sampled by the second holding unit 263 and held therein. Subsequently, the second switch 261b is turned to an OFF state (φSH2: Low), and then the column selection switch 254 of the column <1> is turned to an OFF state (φHCLK<1>: Low). A period during which the second switch 261b is in the ON state (sampling period) is shorter than a period during which the column selection switch 254 of the column <1> is in the ON state (transfer period).

Thereafter, when a driving signal (φMUXSEL: High) is supplied from the timing generator 25 to the multiplexer 266, the multiplexer 266 outputs the imaging signal held in the second holding unit 263 to the output unit 267.

Subsequently, the horizontal resetting transistor 256 is turned to an ON state (φHCLR: High) in a pulsed manner to reset the horizontal transfer line 258 again. While the horizontal resetting transistor 256 is in the ON state, the output of the driving signal to the multiplexer 266 ends (φMUXSEL: Low). Thereafter, the horizontal resetting transistor 256 is turned to an OFF state (φ: Low).

Next, by turning the column selection switch 254 of the column <2> to an ON state (φHCLK<2>: High), an imaging signal of the column <2> is transferred to the horizontal transfer line 258. Thereafter, by turning the second switch 261b to the ON state (φSH2: High), the imaging signal is sampled by the second holding unit 263 and held therein. Subsequently, the second switch 261b is turned to the OFF state (φSH2: Low), and then the column selection switch 254 of the column <2> is turned to an OFF state (φHCLK<2>: Low). Thereafter, the multiplexer 266 performs an operation to output the imaging signal held in the second holding unit 263 to the output unit 267. The operation is the same as the operation to output the imaging signal described for the column <1>.

The imaging unit 20 repeats the operations for each column as many times as the number of columns of the light-receiving unit 23 (or the number of columns required to read), thereby outputting the imaging signals for one line.

When the imaging signals for one line have been output, the variable voltage VR is adjusted to be a Vfd_L level (for example, 1 V). Next, while keeping the variable voltage VR at the Vfd_L level, the driving signal φR<0> is applied in a pulsed manner to a gate of the pixel resetting unit 236 of the selected pixel row <0>. Consequently, the deselection voltage Vfd_L is applied to the gate of the pixel source-follower transistor 237 of the pixel row <0>, and the pixel source-follower transistor 237 is turned to an OFF state. Through the above processes, the unit pixel 230 included in the pixel row <0> is deselected (deselection operation).

By repeating the reading operation for one line as many times as the number of the unit pixel rows (or the number of rows required to read), imaging signals for one frame are output. Through the above operations, a black reference signal is positioned at the head of signal output of each row. A black reference signal corresponding to a plurality of columns is temporarily stored and subjected to averaging in the imaging signal processing unit 52. Thereafter, a noise component is extracted therefrom, and the extracted noise component is used for eliminating a noise component included in the imaging signal.

According to the first embodiment described above, the buffer 26 separately holds the reference signal and the imaging signal, sequentially switches between the signals and outputs the switched signals, whereby a read time of an OB region can be shortened. As a result, a frame rate of the imaging signal can be improved.

In addition, according to the first embodiment, the read time of the OB region can be shortened. Consequently, in a case where the image sensor (first chip 21) includes CMOS, distortion of an image caused by a rolling shutter can be reduced.

In addition, according to the first embodiment, the reading unit 24 reads each of the reference signal generated by the reference signal generation unit 248 and the imaging signal generated by the unit pixel 230, whereby each of the reference signal and the imaging signal changes in the same manner even when there is a variation in the signals upon manufacturing. Therefore, the imaging signal can be accurately corrected based on the reference signal. As a result, improvement in image quality can be realized.

In addition, according to the first embodiment, the reference signal generation unit 248 without a photoelectric conversion element 231 (photodiode) is provided independently from the columns of the unit pixel 230, and the black reference signal is read only a predetermined number of times (two or more times) from the reference signal generation unit 248 before reading a signal of each row of the unit pixel 230. Therefore, the black reference signal corresponding to a plurality of columns is positioned at the head of the signals of each row. By using the black reference signal on the side of the imaging signal processing unit 52, reduction of horizontal lines or the like can be performed. Therefore, improvement in image quality can be realized.

In addition, according to the first embodiment, the reference signal generation unit 248 is not provided with the photoelectric conversion element 231. Therefore, there is no need to provide a light shielding sheet or the like to output the black reference signal. Furthermore, since the reference signal generation unit 248 does not originally have a configuration which responds to light, there is no need to provide the reference signal generation unit 248 over a plurality of columns in order to eliminate an influence of the leakage of light. Therefore, size reduction of the imaging unit 20 can be realized as well as improvement in image quality.

In addition, according to the first embodiment, since the imaging unit 20 transmits the black reference signal generated by the reference signal generation unit 248 to the connector unit 5 when moving from a horizontal blanking period to an imaging signal period, occurrence of fluctuations in the power supply voltage, which is caused by fluctuations in power consumption, can be suppressed. Therefore, deterioration of the image quality caused by fluctuations in the power supply can be suppressed.

In the first embodiment, the reference signal generation unit 248 is provided on the first vertical line in the light-receiving unit 23. However, the reference signal generation unit 248 may be provided, for example, on the last vertical line in the light-receiving unit 23.

Second Embodiment

Next, a second embodiment of the present invention will be described. An endoscope system according to the second embodiment has a similar configuration to the endoscope system 1 according to the first embodiment, and is different from the first embodiment in a configuration of a first chip of an imaging unit (imaging device) and an operation of the imaging unit. Therefore, hereinbelow, the configuration of the first chip in the imaging unit according to the second embodiment will be described, and then the operation of the imaging unit will be described. The same reference signs are given to the same elements as those of the endoscope system 1 according to the first embodiment, and the explanation thereof will be omitted.

Configuration of First Chip

Figure 8:
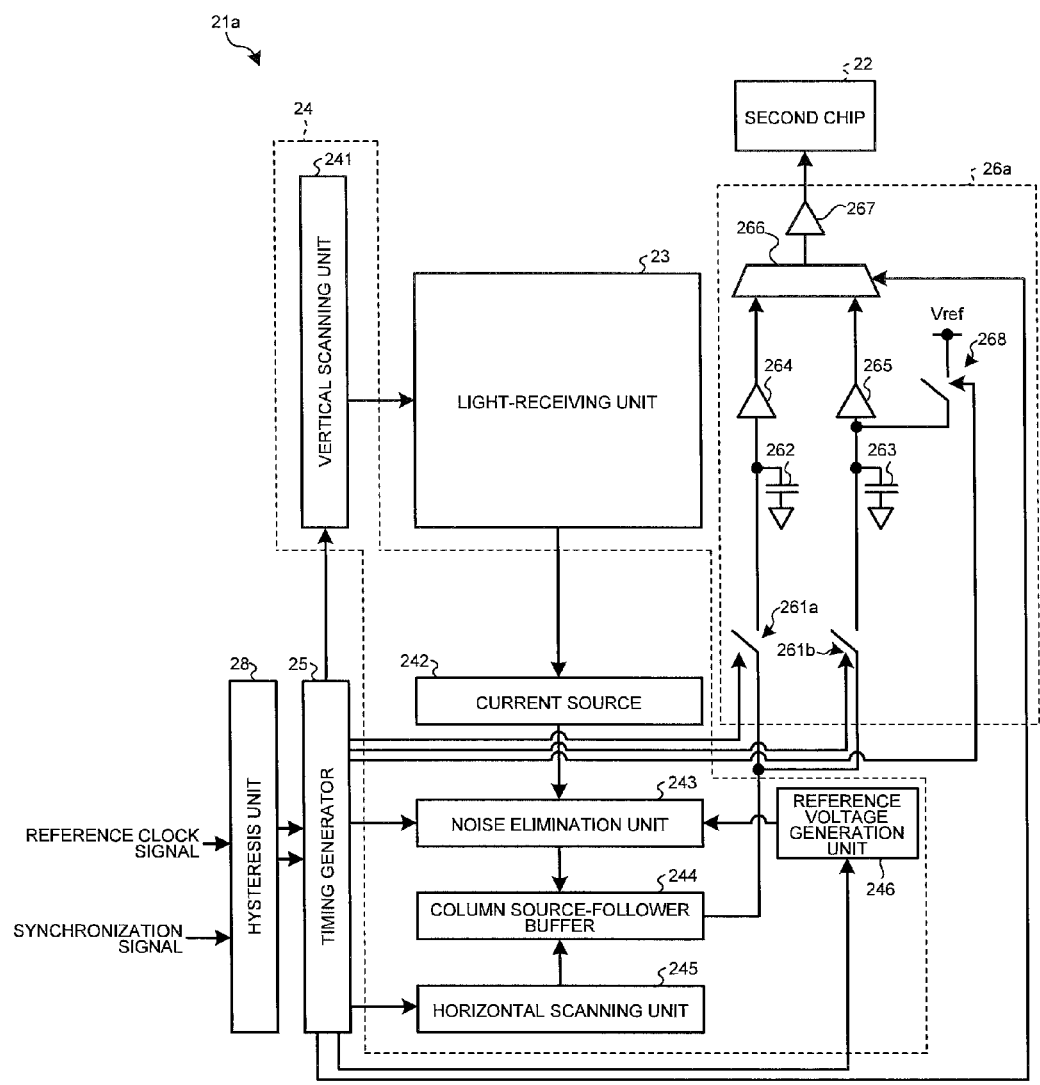
FIG. 8 is a block diagram illustrating a detailed configuration of a first chip in an imaging unit according to a second embodiment of the present invention.
Figure 9:
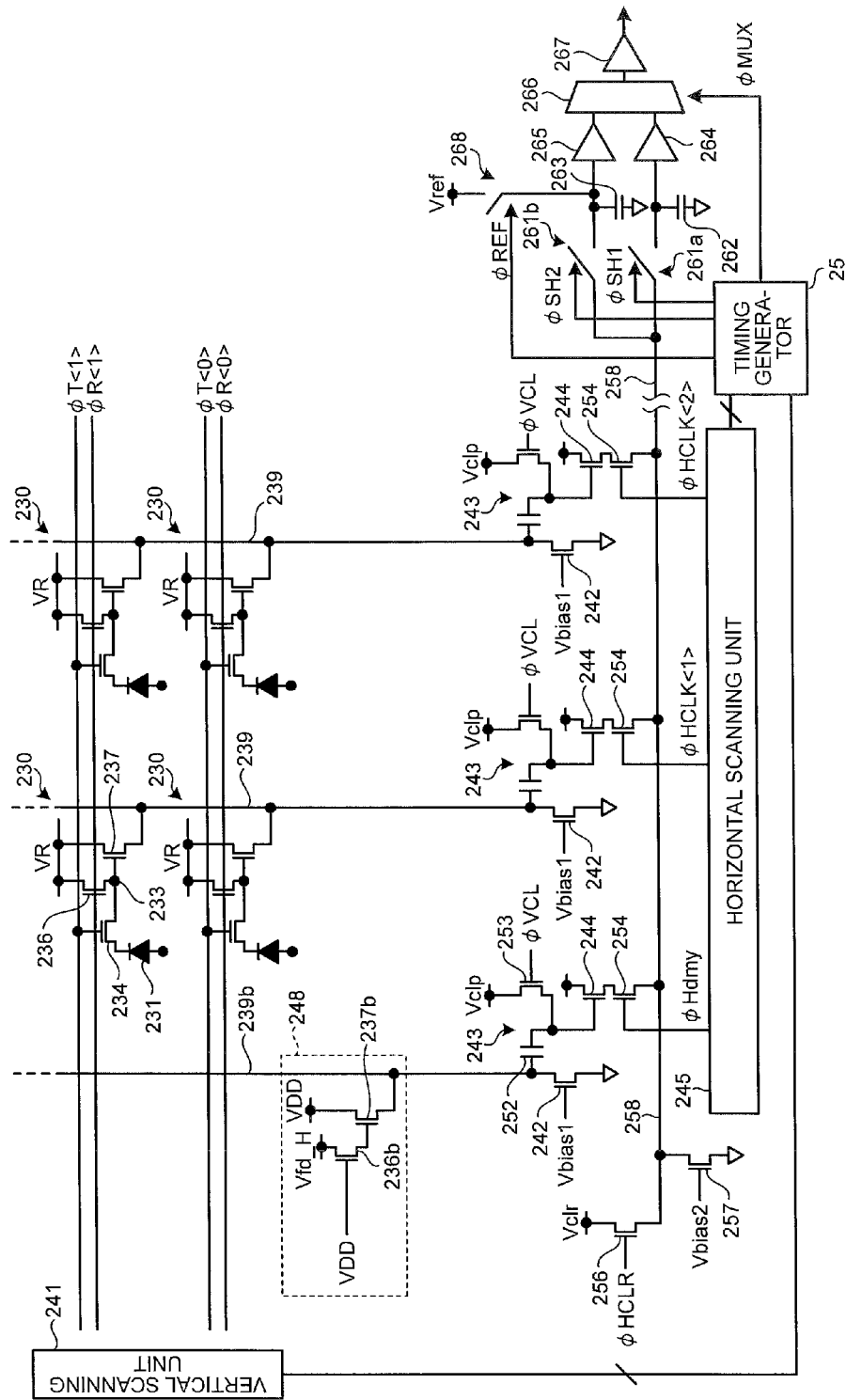
FIG. 9 is a circuit diagram illustrating a configuration of the first chip in the imaging unit according to the second embodiment of the present invention.

FIG. 8 is a block diagram illustrating a detailed configuration of a first chip 21a in an imaging unit 20a according to the second embodiment. FIG. 9 is a circuit diagram illustrating the configuration of the first chip 21a.

As illustrated in FIGS. 8 and 9, the first chip 21a includes a light-receiving unit 23, a reading unit 24 (driving unit), a timing generator 25, a buffer 26a, and a hysteresis unit 28.

The buffer 26a includes a sample holding switch 261, a first holding unit 262, a second holding unit 263, a first operational amplifier 264, a second operational amplifier 265, a multiplexer 266, an output unit 267, and a resetting unit 268.

The resetting unit 268 is provided between the second holding unit 263 and the multiplexer 266, and resets the second holding unit 263 after the multiplexer 266 has output the reference signal held by the first holding unit 262. Here, "to reset the second holding unit 263" means "to reset an amount of charge stored in the second holding unit 263 to an amount of charge corresponding to a reference voltage Vref (Q=C2·Vref)". Hereinbelow, the resetting operation is also referred to as "to reset a voltage of the second holding unit 263 to the reference voltage Vref".

Operation of Imaging Unit 20a

Next, a drive timing of the imaging unit 20a will be described.

Figure 10:
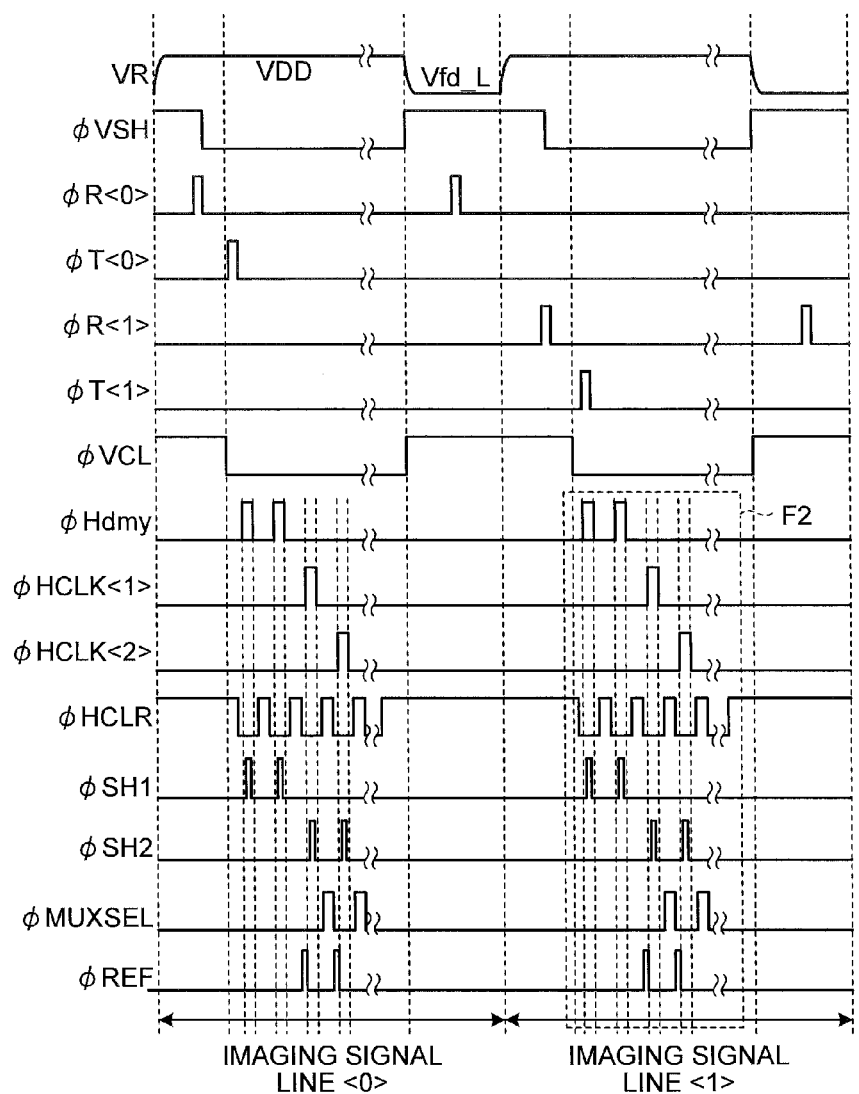
FIG. 10 is a timing chart illustrating a drive timing of the imaging unit according to the second embodiment of the present invention.
Figure 11:
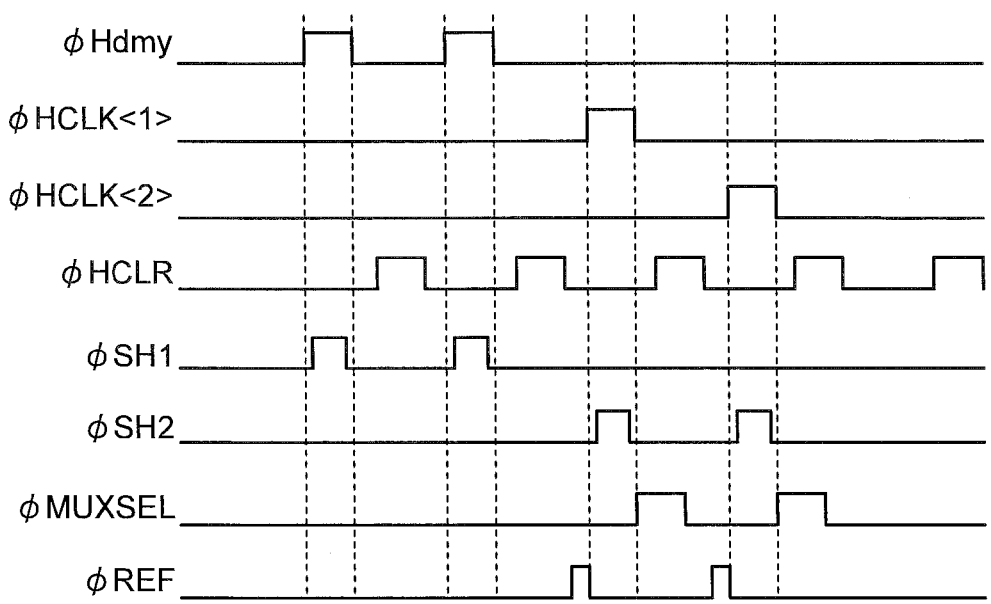
FIG. 11 is a timing chart illustrating an enlarged region of FIG. 10.

FIG. 10 is a timing chart illustrating the drive timing of the imaging unit 20a. FIG. 11 is a timing chart illustrating an enlarged region F2 of FIG. 10. In FIGS. 10 and 11, a variable voltage VR, a driving signal φVSH, and driving signals φR, φT, φVCL, φHdmy, φHCLK, φHCLR, φSH1, φSH2, φMUXSEL, and φREF are illustrated sequentially from the top. In FIGS. 10 and 11, the driving signals φR and φT are signals in cases where the row <M> is <0> and <1>, and the driving signal φHCLK is a signal in cases where the column <N> is <1> and <2>.

In the second embodiment, the operations, which are performed by the imaging unit 20a and include from the operation for setting the variable voltage VR to the operations for reading the reference signal (black reference signal) a predetermined number of times (in FIGS. 10 and 11, twice) and outputting the signal, are the same as those described in the first embodiment (see, FIG. 6).

Thereafter, the imaging unit 20a reads the reference signal (black reference signal) a predetermined number of times and outputs the signal, then turns the resetting unit 268 to an ON state (φREF: High), and resets the voltage of the second holding unit 263 to the reference voltage Vref. Subsequently, the imaging unit 20a performs an operation for reading and outputting an imaging signal of a column <1> in the same manner as in the first embodiment.

The imaging unit 20a sequentially performs the operation for the column <1> described above with respective to all columns required to read, thereby outputting the imaging signals for one line. Thereafter, the imaging unit 20a performs a deselection operation of a unit pixel 230 included in a pixel row <0>.

By repeating the reading operation for one line as many times as the number of the unit pixel rows (or the number of rows required to read), imaging signals for one frame are output. Through the above operations, a black reference signal is positioned at the head of signal output of each row. The black reference signal is used to eliminate a noise component included in the imaging signal, which is the same as the case of the first embodiment.

According to the second embodiment described above, the buffer 26a separately holds the reference signal and the imaging signal, sequentially switches between the signals and outputs the switched signals, whereby a read time of an OB region can be shortened. As a result, a frame rate can be improved.

In addition, according to the second embodiment, since a resetting unit 29 resets the voltage held by the second holding unit 263 to the reference voltage after the reference signal held by the first holding unit 262 has been output, noiseless imaging signals can be sequentially output.

According to some embodiments, it is possible to shorten a read time in an OB region.

As described above, the present invention may include various embodiments not described herein, and various design changes and the like can be performed in the scope of technical ideas specified by the claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image sensor comprising:
    a plurality of pixels disposed in a two-dimensional matrix form and configured to receive light from outside, and to generate an imaging signals in accordance with an amount of the received light and output the imaging signals to first vertical transfer lines to which corresponding ones of the plurality of the pixels are connected;
    a reference signal generation circuit provided independently from the plurality of pixels and configured to generate a reference signal in accordance with a predetermined voltage and output the reference signal to a second vertical transfer line provided dedicatedly to the reference signal generation circuit;
    a transfer circuit comprising:
        a first noise elimination circuit provided in the second vertical transfer line and configured to perform noise elimination on the reference signal output from the reference signal generation circuit; and
        second noise elimination circuits provided in corresponding ones of the first vertical transfer lines and configured to perform noise elimination on the imaging signals output from the plurality of pixels,
        wherein the transfer circuit is configured to transfer the reference signal after the noise elimination performed by the first noise elimination circuit and the imaging signals after the noise elimination performed by the second noise elimination circuits, during different periods; and
    an output circuit configured to separately hold the reference signal and the imaging signals transferred from the transfer circuit, and sequentially switch between the reference signal and the imaging signals to output the switched signal.

2. The image sensor according to claim 1,
    wherein the output circuit comprises:
        a first holding circuit configured to hold the reference signal;
        a second holding circuit configured to hold the imaging signal; and
        a switching circuit connected to each of the first holding circuit and the second holding circuit, and configured to sequentially switch between the reference signal held by the first holding circuit and the imaging signal held by the second holding circuit to output the switched signal.

3. The image sensor according to claim 2, further comprising a resetting circuit provided between the second holding circuit and the switching circuit, and configured to reset the first holding circuit after the switching circuit outputs the reference signal held by the first holding circuit.

4. The image sensor according to claim 2,
    wherein the first holding circuit comprises a first capacitor configured to hold an amount of charge corresponding to a signal level of the reference signal,
    wherein the second holding circuit comprises a second capacitor configured to hold an amount of charge corresponding to a signal level of the imaging signal, and
    wherein a capacitance of the first capacitor is larger than a capacitance of the second capacitor.

5. The image sensor according to claim 1, wherein the reference signal is a black reference signal for determining a black level of the imaging signal.

6. The image sensor according to claim 2,
    wherein the reference signal generation circuit is configured to generate the reference signal each time the imaging signal for each pixel row is generated, and
    wherein the switching circuit is configured to switch between the reference signal and the imaging signal for each pixel to output the switched signal.

7. An imaging device comprising the image sensor according to claim 1.

8. An endoscope comprising:
    an insertion unit; and
    the imaging device according to claim 7 arranged at a distal end side of the insertion unit.

9. An endoscope system comprising:
    the endoscope according to claim 8; and
    a processor comprising hardware configured to convert the imaging signal output from the output circuit to an image signal.

* * * * *